(12) United States Patent
Raffer

(10) Patent No.: US 9,261,446 B2
(45) Date of Patent: Feb. 16, 2016

(54) ROTATIONAL VISCOMETER

(75) Inventor: Gerhard Raffer, Graz (AT)

(73) Assignee: Anton Paar GmbH, Graz-Strassgang (AT)

( * ) Notice: Subject to any disclaimer, the term of this patent is extended or adjusted under 35 U.S.C. 154(b) by 371 days.

(21) Appl. No.: 13/502,810

(22) PCT Filed: Oct. 13, 2010

(86) PCT No.: PCT/AT2010/000391
§ 371 (c)(1),
(2), (4) Date: Apr. 19, 2012

(87) PCT Pub. No.: WO2011/047397
PCT Pub. Date: Apr. 28, 2011

(65) Prior Publication Data
US 2012/0210774 A1    Aug. 23, 2012

(30) Foreign Application Priority Data
Oct. 22, 2009   (AT) ................................ A 1669/2009

(51) Int. Cl.
*G01N 11/10* (2006.01)
*G01N 11/14* (2006.01)

(52) U.S. Cl.
CPC ...................... *G01N 11/14* (2013.01)

(58) Field of Classification Search
CPC ................................ G01N 11/10; G01N 11/14
USPC ........................................................ 73/54.28
See application file for complete search history.

(56) References Cited

U.S. PATENT DOCUMENTS 3,572,086 A    3/1971   Johnston
5,503,003 A *  4/1996   Brookfield ............ G01N 11/14
                                                   73/54.28

FOREIGN PATENT DOCUMENTS

GB     683 031 A    11/1952
GB     810 242 A    3/1959
GB     2 204 701 A  11/1988

* cited by examiner

*Primary Examiner* — Laura Martin
*Assistant Examiner* — Alex DeVito
(74) *Attorney, Agent, or Firm* — Laurence A. Greenberg; Werner H. Stemer; Ralph E. Locher

(57) ABSTRACT

A rotational viscometer contains a measuring shaft that can be rotated at a specified rotational speed, a measuring part that is carried by the measuring shaft and that can be lowered into a sample, and a detection unit for determining the angle of torsion of the measuring part relative to the driven part of the measuring shaft. Accordingly, a twistable element is inserted into the measuring shaft, preferably in the section of the measuring shaft close to a motor. The detection unit is moved along with the shaft and determines the relative twist or the angle of torsion (twist) between the shaft part located on the motor side relative to the twistable element and the shaft part located on the measuring-part side. The output signals of the detection unit are fed to an evaluation device as the basis for determining the viscosity of the sample.

20 Claims, 4 Drawing Sheets

ROTATIONAL VISCOMETER

BACKGROUND OF THE INVENTION

Field of the Invention

The invention relates to a rotational viscometer.

With rotational viscometers, the viscosity of samples is determined over wide measuring ranges with sufficient accuracy by rotation of measuring parts in any measuring vessels located beneath the viscometer which contain the sample.

Such viscometers are proposed for example in accordance with ASTM D2983 for testing lubricants in the automobile industry, and are known as Brookfield viscometers in terms of principle from U.S. Pat. No. 2,679,750.

In such case, the viscosity of a sample is determined by rotation of a standardised measuring part in the sample to be measured. Measuring parts are known for example from ASTM D5133-96.

The measuring part is generally fastened detachably and hence exchangeably to the measuring shaft which is rotated by a motor, is dipped into the sample and caused to rotate by means of the motor and measuring shaft. Owing to its viscosity, the sample in the measuring vessel counteracts this movement of the measuring part in a braking manner. The drive shaft to which the measuring part is fastened is twisted or can be equipped with a resilient element which counteracts the rotation, the torque which counteracts the rotary movement leading to torsion of the shaft or to deflection of this resilient element. The angle which occurs is determined by suitable sensors; this angle is a measurement of the viscosity of the sample.

In contrast to precision rheometers or absolute measuring viscometers with exactly defined test geometries, e.g. with a shear gap with defined gap geometry between two measuring parts, and hence also defined shear conditions, here the measuring part or measuring body dips into the liquid sample, the geometry of the beaker being ignored. Accurate determination of the shear rate in this case is not possible.

The results are thus relative viscosity values, which depend on the measuring parts used just as much as on the flow in the sample which occurs, e.g. eddying changes the measurement results by preventing laminar flow. In the individual case, different surfaces, e.g. sand-blasted or profiled measuring parts, are used in order to prevent the formation of sliding layers. Nevertheless, these viscometers are tried and tested aids for quality control in many fields of application, e.g. the foodstuffs industry, cosmetics industry or dyestuffs industry, for checking the viscosity of samples, e.g. for maintaining standard conditions.

The make-up of a viscometer comprises in principle a motor with an exact constant specified rotational speed which drives a measuring shaft, sensors for measuring the angle of rotation, at the lower end of the measuring shaft a measuring part and also a stand which bears the motor, shaft and measuring part and optionally has means for vertical adjustment. The measuring part dips into the sample as far as a defined dip mark, the sample being located in any container whatsoever.

Different arrangements of resilient elements are known for measuring the torque directed against the rotating movement by the resistance of the sample.

In precision equipment, the torque measurement generally takes place by means of the power consumption I of the driving electric motor, and in this case, depending on the motor or apparatus type used, for the torque M:

$M = c_1 \cdot I$ or $M = c_2 \cdot I^2$ with equipment-specific constants $c_1$ or $c_2$ respectively.

In simple, inexpensive apparatus, a spring element is used for measuring torque, e.g. coil springs or spring wires. These torsion elements exhibit a deflection path s or a deflection angle which is proportional to the applied force F or to the torque.

Hooke's law of elasticity applies, $F = c_H \cdot s$, with $c_H$ being equal to Hooke's spring constant.

These mechanical force transducers are less accurate than the measurement of the power consumption of the measuring motors, because they always also detect the behaviour of the force sensor itself as well, and relatively large deflections are necessary to obtain a signal which can be evaluated at all. Therefore they are only used in simpler, inexpensive relative viscometers.

Such spring elements do not have sufficient strength in the direction of the axis of rotation, i.e. in the direction of the z-axis; the measuring shaft with spring therefore has to be rotatably mounted and supported in order to permit the measurement.

Measurement of the torque in the known Brookfield viscometer takes place via a coil spring. Since the latter is not stable in the z-direction, the shaft has to be mounted separately on a friction bearing and above it the torque of the sample counter to the rotation has to be measured. This mounting however generally results in distortion of the measurement results due to the bearing friction. The use of bearings which are as friction-free as possible, for example toe bearings, makes the measuring equipment more expensive and complicates it. Furthermore, the measuring range of this equipment is limited: only angular resolutions which fit with the spring constant of the spring used in each case can be measured.

Mostly, in the known embodiments means, such as for example a "bar", which permit determination of the angle of rotation which occurs, are located on the drive shaft above the resilient connection to the measuring shaft or to the measuring part. The angle of rotation is proportional to the torque, or there is a functional connection between the torque and the angle of rotation. The torque with which the sample counters the movement of the measuring body is thus a measurement of the viscosity of the sample. Arrangements with torsional axes, e.g. piano wire, are also known, but offer only inadequate stability.

BRIEF SUMMARY OF THE INVENTION

It is an object of the invention to construct a rotational viscometer which has as broad as possible a range of use, is of simple construction and supplies precise measured values. Changes in length of the measuring shaft and an associated distortion of measuring shafts the torsion of which is measured should be avoided. A sensitive arrangement which is as compact as possible should be produced.

This is achieved according to the invention in a rotational viscometer with a measuring shaft which can be rotated at a specified, in particular constant, rotational speed, a measuring part which is borne thereby and can be lowered into a sample, and a detection unit for determining the torsion angle of the measuring part relative to the driven part of the measuring shaft, in that a twistable element is inserted into the measuring shaft, preferably in its section close to the motor, in that the relative twisting or the torsion angle between the shaft part located on the motor side with respect to the twistable element and the shaft part located on the measuring-part side is determined, and in that the output signals of the detection unit are supplied to an evaluation means as base values for determining the viscosity of the sample. The detection unit is moved jointly with the measuring shaft.

In the rotational viscometer according to the invention, the twistable element inserted into the measuring shaft means that the torsional moment exerted by the measuring part on the measuring shaft acts only on a special region of the measuring shaft which is arranged therefor, and the twisting of the measuring part relative to the motor or the part of the measuring shaft which is on the motor side takes place there. The twistable element is formed to be sensitive to torsion and is not influenced by changes in length of the shaft parts located above and below which are due to heat.

It has proved advantageous if a flexural pivot or a torsion rod is used as twistable element and/or if an inductive, a capacitive or an optical measuring sensor is provided as detection unit. Such twistable elements offer the necessary sensitivity and yield precise, reproducible measured values.

An arrangement which yields particularly exact measured values is yielded if, in a flexural pivot having sleeves which can be twisted relative to one another, one of the measuring-sensor parts is fastened to the end of the one sleeve and the other measuring-sensor component is fastened to the end of the other sleeve in each case.

When selecting a twistable element, it is expedient if the twistable element is formed to be rigid in the axial direction of the measuring shaft. Thus distortion of measurement results by a movement of the measuring shafts in the axial direction is largely ruled out.

A compact and sensitive construction is achieved if provision is made for the detection unit to have two opposing measuring-sensor parts which cooperate with one another, e.g. two capacitor plates, two coils or two screens provided with light holes, the one measuring-sensor part being connected, preferably directly, to the shaft part of the measuring shaft which is on the motor side and the other measuring-sensor part being connected, preferably directly, to the shaft part of the measuring shaft which is on the measuring-part side.

In order to rule out influences of external nature or from the surroundings on the shaft parts, it is advantageous if the two measuring-sensor parts are fastened in each case to a shaft part in the immediate vicinity, in particular one measuring-sensor part immediately above and one measuring-sensor part immediately below, the twistable element.

A simple, easily produced and sensitive construction is yielded if a capacitive detector unit is provided which comprises as measuring-sensor parts two, in particular disc-shaped, capacitor plates, the opposing surfaces of the capacitor plates being coated with metal layers which form preferably radially extending surface regions or crosspieces, and that a measuring unit for determining the changes in capacitance of the capacitor formed by the two plates during the course of mutual rotation of the two plates is provided, with provision optionally being made for two capacitor surfaces which are segmented or intermesh in a finger-shape to be formed on each of the plates, or for at least one metal layer forming [a] capacitor surface to be applied to each of the two plates, and/or in that the capacitor surface(s) which is (are) formed on the respective plate are connected into a bridge circuit.

A further simplification of the construction in particular with regard to compactness and secured transmission of measurement data is yielded if a transceiver component or transmitter is borne by one measuring-sensor part, preferably the upper one or the one located on the motor side, and/or one shaft part, preferably the one on the motor side, for picking up the energy necessary for measuring, which takes place via an air gap, and for emitting the measuring signals to a transceiver on the equipment side, which takes place via an air gap. It is further advantageous if jointly moved coils for coupling-in of energy and optionally data transmission are borne by the upper or motor-side measuring-sensor part and/or the motor-side shaft part, which coils cooperate with field coils located on the stand or housing of the viscometer. In such case, it is advantageous, from the point of view of the construction, if at least the twistable element and/or the coils which are moved jointly with the shaft and/or the measuring-sensor parts are arranged in the region or at least partially or entirely beneath the space provided for bearing the measuring shaft or the shaft part on the motor side.

If provision is made for the output signals of the detector unit to be transmitted via a transmitter in contact-free manner or via an air gap to the receiving or evaluation unit located on the housing side, or for the values determined by the detection unit to be processed therein and the resulting viscosity values or processed measured values for determining the viscosity values to be transmitted via the transmitter in contact-free manner or via an air gap to a receiving or evaluation unit located on the housing side, the advantage is obtained that a rotational viscometer which is largely not influenced by environmental effects is provided which can be operated without external intervention or without the arrangement of disruptive lines.

The rotational viscometer according to the invention is suitable for use with extremely high torques, in which use error influences of friction and angular resolution do not play too large a part, but the arrangement requires sufficient rigidity of the twistable element. However, the viscometer according to the invention, owing to its high-resolution determination of position and angle, also provides picking-up of measured values such as are permitted by complicatedly mounted pick-ups, without arrangements which are as friction-free as possible for mounting the measuring shaft or jewel bearings used being required. It is merely necessary to use a drive motor with an exactly settable rotational speed, and to determine the angle of rotation via a twistable element. It is advantageous in this case if the resilient element is formed to be as rigid as possible in the z-direction and is kept as short as possible in the z-direction, or is formed to be as rigid as possible against tilting in the radial direction.

The flexural pivot which can be used according to the invention is sensitive to the slightest changes in torque, and is arranged beneath the bearing of the measuring shaft, that is to say beneath the bearing which bears the shaft part which is close to the motor, and thus measures purely the counter-torque of the sample. Further influences can be ruled out if the components for determining position or angle are moved or turned jointly with the shaft, or the measured values for the angle of rotation are read out in contact-free manner. The influence of errors on the measurement result due to the mounting of the measuring shaft does not occur. Further environmental effects are ruled out if the necessary sensors are arranged directly on the twistable element for measuring the angle of rotation which occurs.

If a capacitive angle measurement is used, this permits permanent reading-out of the measured values of the torsion of the twistable element or of the torsion angle of the measuring part. The spring action, which is rigid in the direction of the z-axis or in the direction of the axis of rotation of the shaft parts, of a flexural pivot or a torsion rod permits a robust construction and the attachment of the two measuring-sensor parts which cooperate with one another closely opposite one another directly above and below the twistable element. The position measurement which is thereby of high resolution, with the capacitive angle measurement of high resolution, in particular if the capacitor covering takes place in the form of segments and the measurement surfaces are connected into a double bridge, permits a measurement across a large rotational speed or viscosity range.

The invention will be explained in greater detail below with reference to the drawings.

Figure 6:
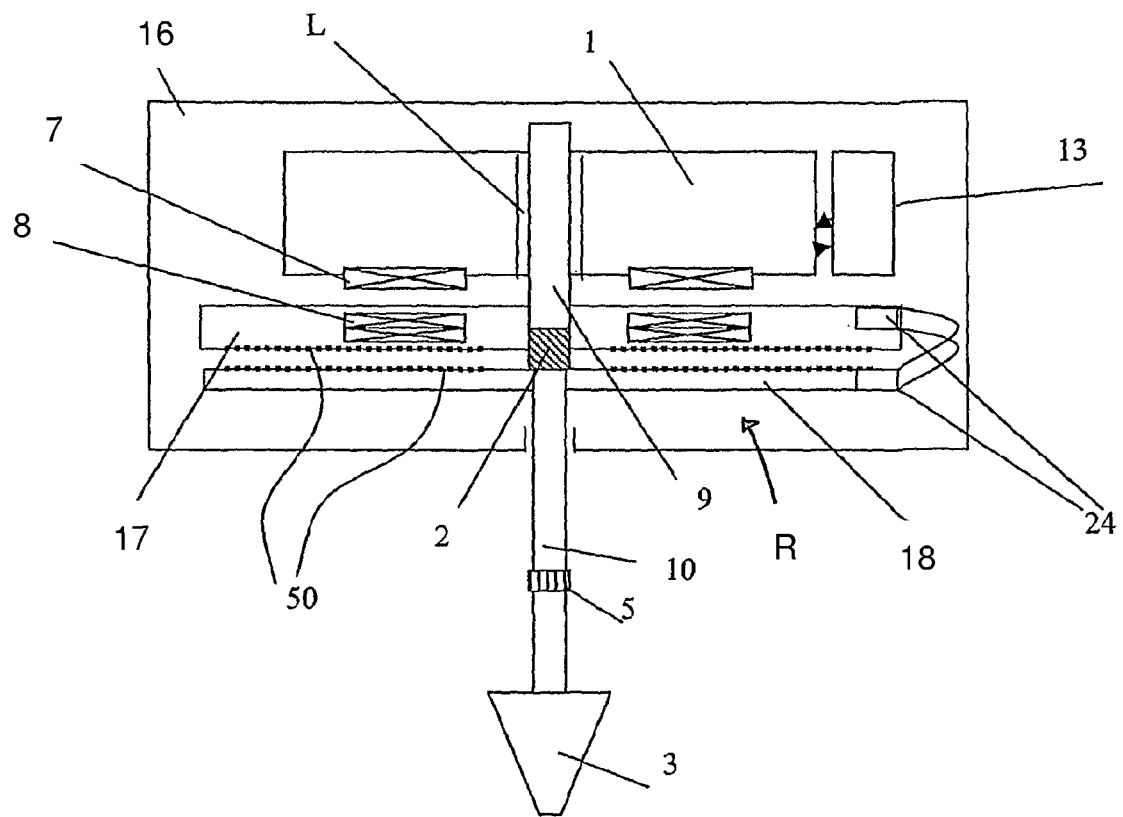

A particularly compact construction is illustrated in FIG. 6.

DESCRIPTION OF THE INVENTION

Figure 1:
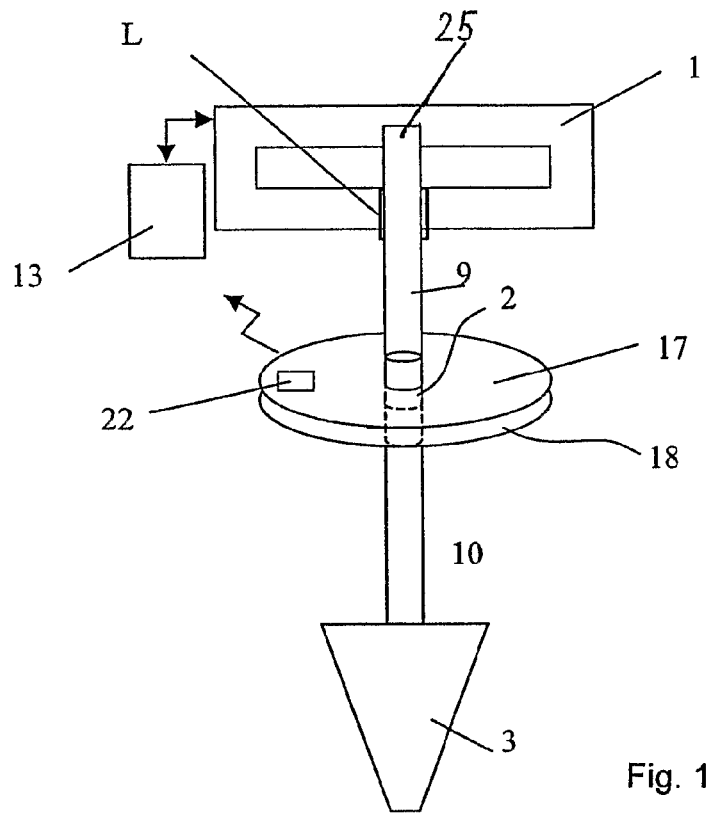
FIG. 1 shows a schematic diagram of a rotational viscometer.

The rotational viscometer diagrammatically illustrated in FIG. 1 has a unit with a drive motor 1 and a measuring shaft 25 which is driven thereby. The measuring shaft 25 comprises in its region close to the motor a shaft part 9 adjoining the motor, which part bears a twistable element 2. The element 2 bears a lower shaft part 10 which bears the measuring part 3. Above and below the twistable element 2 there are arranged measuring-sensor parts 17, 18. The upper measuring-sensor part 17 bears a transmitter 22, with which the measured values relating to twisting of the twistable element 2 or of the upper and lower measuring part relative to one another are transmitted to an evaluation/receiving unit. During a measurement, the motor 1 rotates the measuring shaft 25 at a specified rotational speed. Owing to the friction exerted by the sample on the measuring part 3 owing to its viscosity, the measuring part 3 lags behind by a given angle. This torsion angle is determined with the measuring-sensor components 17, 18 and is transmitted to the evaluation unit 13. This transmission advantageously takes place in wireless manner. This embodiment represents a relatively simple embodiment of a rotational viscometer according to the invention.

Figure 2:
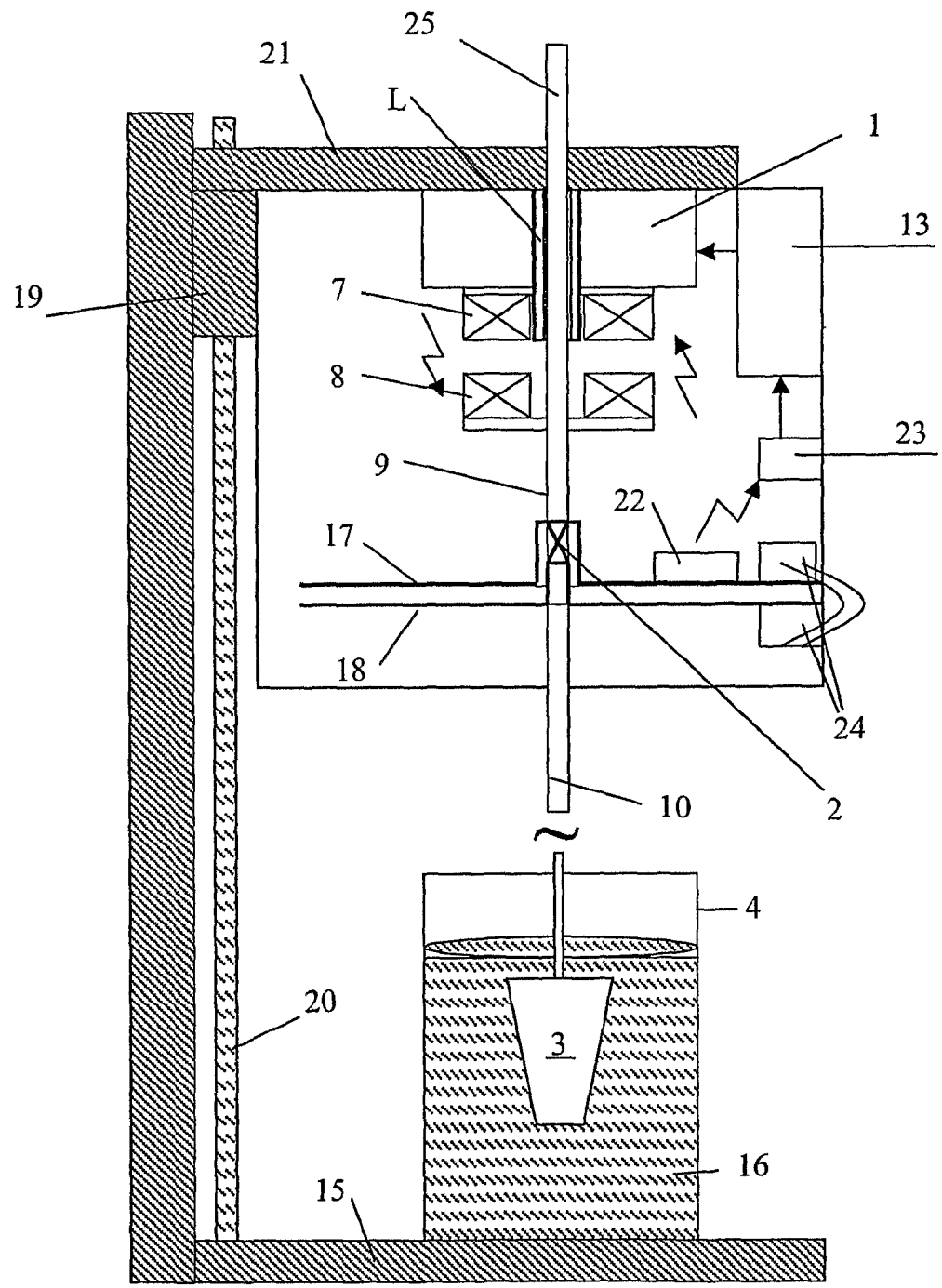
FIG. 2 shows a diagrammatic sectional view of a rotational viscometer according to the invention.

FIG. 2 shows diagrammatically a rotational viscometer, with a stand in which a support 21 is vertically adjusted with a spindle 20 by rotating the spindle 20 in a spindle nut 19. The support 21 bears a motor 1 which rotates the drive shaft or measuring shaft 25 at a specified rotational speed. This motor may for example be formed by electric coils 7 which cooperate with coils 8 borne by the drive shaft or measuring shaft 25 or the upper shaft part 9 and drive them in contact-free manner by excitation. The measuring shaft 25 can be mounted in a bearing L of known construction (air bearing, friction bearing etc.). Generally the mounting of the shaft which is usual in the drive motors is sufficient. A control and evaluation unit 13 imparts the corresponding control commands, in particular with regard to rotational speed and direction of rotation to the motor 1.

The measuring shaft 25 is interrupted by a twistable element 2 for measuring torque which is inserted between the upper shaft part 9 and the lower shaft part 10 and permits relative twisting of the measuring parts 9, 10 with respect to the axis of rotation. The lower shaft part 10 bears the measuring part 3, if need be via coupling devices. The measuring part 3 is lowered into a measuring vessel 4 with a sample 16.

Just above the twistable element 2 there is arranged a first measuring-sensor part 17 and just below the twistable element 2 a further measuring-sensor part 18. The upper measuring-sensor part 17 is fastened to the upper shaft part 9 of the measuring shaft 25 or to the end of the twistable element 2 which is close to this shaft part 9. The further measuring-sensor part 18 is fastened to the lower end of the twistable element 2 or to the lower shaft part 10 as close as possible to the twistable element 2. Thus any influence of the measuring shaft on the twistable element or the torsion angle which occurs is avoided.

During the course of the measurement, the two measuring-sensor parts 17 and 18 are twisted relative to one another. This twisting or the angle of rotation is sensed with sensors 24 which are located on the measuring-sensor parts 17, 18 or are formed thereby or are part thereof. The results obtained are transmitted either directly or after appropriate evaluation by a transmission unit 22 which is borne by one of the measuring-sensor parts, advantageously by the upper measuring-sensor part 17, to a receiver 23 on the equipment or housing side which supplies the values to the control and evaluation unit 13.

In principle it is also possible for the measured values or the evaluated measured values to be transmitted via the coils 8 borne by the measuring shaft 25 to the field coils 7 on the equipment side or housing side and thence to the control and evaluation unit 13.

Figure 4:
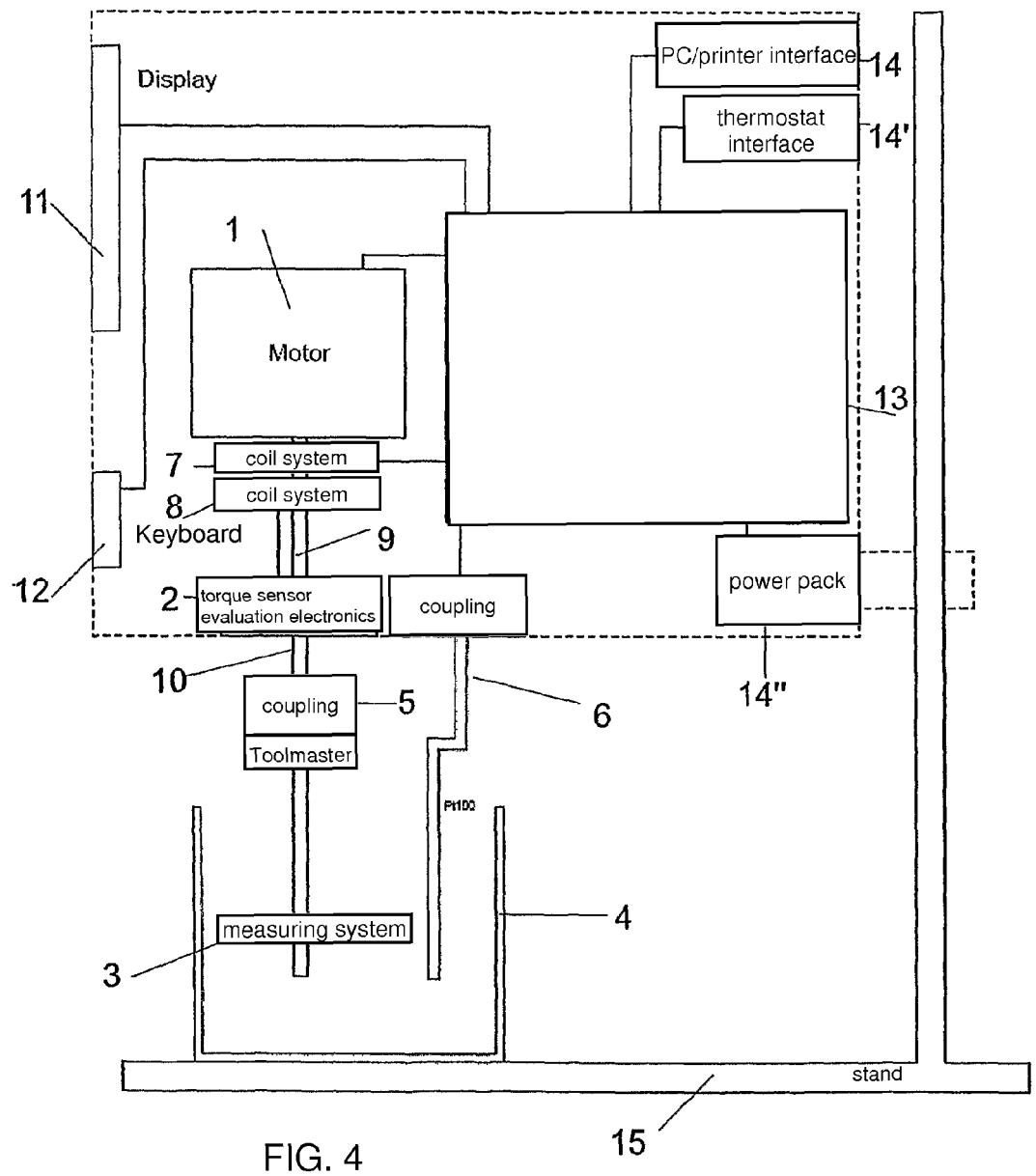
FIG. 4 shows one possible overall construction of a rotational viscometer.

The rotational viscometer illustrated in FIG. 4 has a keyboard 12, in particular a membrane keyboard, for entering or specifying test parameters. A display 11 can show or display the measured values obtained. The control and evaluation unit 13 can output the measured values obtained via a PC/printer interface 14. A power pack 14' serves for supplying power. The control and evaluation unit 13 controls the user interface, the PC/printer interface 14, a thermostat/printer interface 14', if the test is to be performed under constant test conditions or at particular temperatures, the motor 1, the transmission of the measured values, and the temperature of the sample and the surroundings of the sample.

Since according to the invention a mounting which is stable in the z-axis takes place, measurement can be carried out directly on the measuring shaft. Flexural pivots as cylindrical bearings for rotary movements with a limited angle of rotation exhibit great rigidity in the axial and radial direction, whereas the torsional rigidity can be selected dependent on the materials used and spring constants of the leaf springs.

With such flexural pivots, the axis is divided into two parts; the upper and lower parts of the measuring shaft are connected by an articulation which is resilient or exhibits spring characteristics in the direction of rotation. In this case, two sleeves 40, 41 which can be rotated in one another are connected together by at least two leaf springs 42 extending in planes which are perpendicular to one another, as illustrated diagrammatically in FIG. 3.

For determining the relative angle of rotation between the measuring-sensor parts provided, e.g. of parallel discs 17, 18, these measuring-sensor parts or discs are fastened to the sleeves in two neighbouring planes, in particular ones extending parallel to each other and perpendicular to the axis of rotation. Under load, the measuring-sensor parts 17, 18 twist the movable sleeve 41, which is connected to the lower shaft part 10 and the locked-in sleeve 40, which is fastened to the upper shaft part 9, of the flexural pivot relative to each other by an angle which is proportional to the viscosity of the sample, which is detected and evaluated. Suitable measurement methods for determining this angle are e.g. optical or electrical methods.

Figure 3:
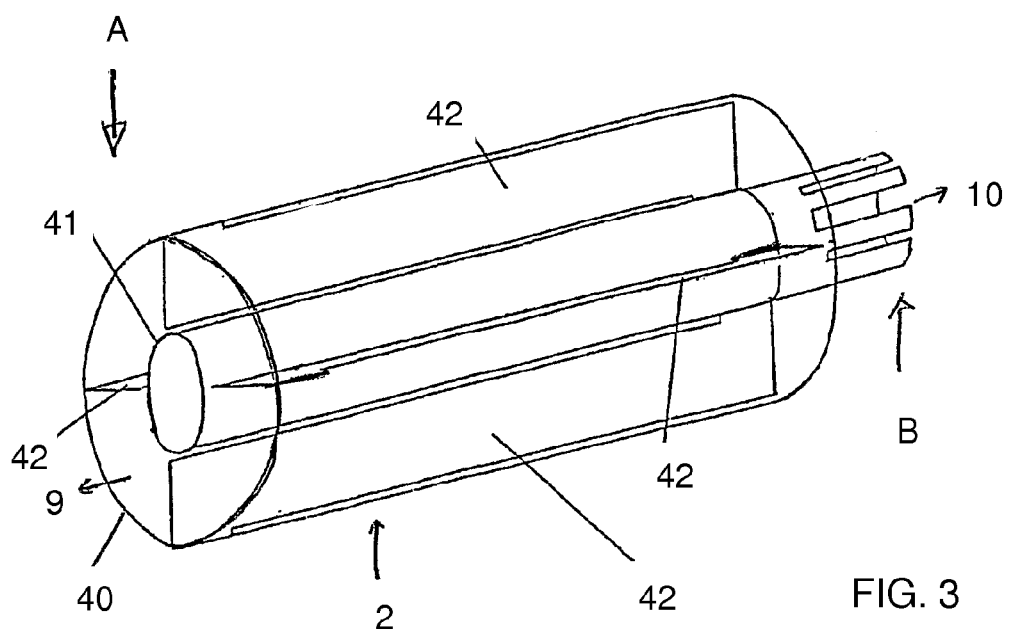
FIG. 3 shows diagrammatically the construction of a flexural pivot used according to the invention.

The flexural pivot 2 illustrated diagrammatically in FIG. 3 is not shown in its use position, in which it usually passes vertically downwards from an upper shaft part 9. A flexural pivot 2 of this type comprises the two sleeves 40, 41 which are mounted to be twistable relative to each other. Between the sleeves 40, 41 extend leaf springs 42, which connect the end of the sleeve 41 located in the region B to the end of the sleeve 40 located in the region A. In the region A, the upper measuring part 9 is connected to the sleeve 40, or the upper measuring-sensor part 17 can be fastened to the sleeve 40. The lower shaft part 10 is fastened to the sleeve 41 in the region B, or the lower measuring-sensor part 18 is fastened in this region of the sleeve 41. The elongate springs react very sensitively to rotation of the sleeves 40 and 41 relative to each other.

In order to obtain extremely accurate results, this measurement should be insensitive to minimal tipping or deflections in the axial direction. This is made possible for example by a capacitive measurement with measuring-sensor parts 17, 18 in the form of capacitor discs in a bridge circuit. However, also other methods such as optical determination of the offset of the two capacitor discs relative to each other or inductive methods are possible.

All the components required for the measurement, such as the full bridge circuit or the components required for the electrical measurement or optical transmission, can be arranged on the two measuring-sensor parts 17, 18 or borne by the measuring shaft 25 or the upper shaft part 9. This means that the motor 1 can jointly turn the parts required for determining the twisting of the measuring axis or the relative twisting of the two shaft parts 9, 10, and the entire measuring arrangement rotates freely with the measuring body 3.

The measured values thus generated of the angle of rotation which is produced are read out in wireless manner and converted into relative viscosity values in accordance with calibration in the attached evaluation unit.

Figure 5:
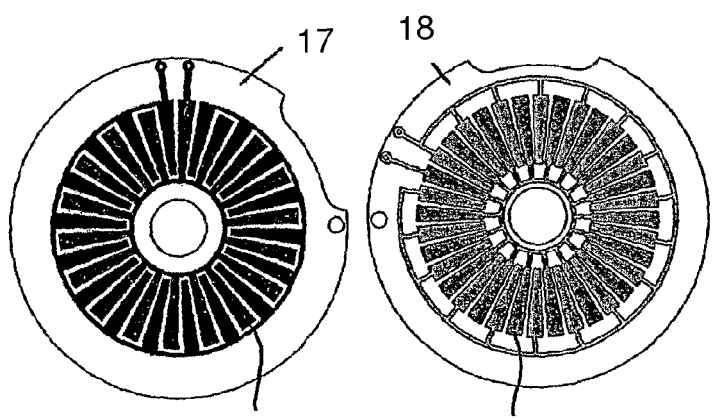
FIG. 5 shows measuring-sensor components in the form of discs with a segmented conductive coating.

In the capacitive measurement illustrated in FIG. 5, two disc-shaped measuring-sensor parts 17, 18 with a segmented conductive coating 50 are mounted parallel to one another on the upper region A or lower region B of a twistable element 2, preferably a flexural pivot. This results in the twisting of the element 2 resulting in twisting of the two discs 17, 18 relative to each other. The capacitances of the two partial segments on the twisting discs change. The conductive coating is divided radially into segments, here for example 36, which are applied to the two discs such that they partially overlap. The capacitances are determined electronically with a bridge circuit; the evaluation therefore takes place not with regard to absolute values of the capacitance, but to the change or relative values of the full bridge.

The electronics react sensitively in this arrangement to change in the overlapping; due to "evening out" the individual segments, the arrangement is however insensitive to a change in spacing or tilting of the discs 17, 18 relative to each other. In contrast to this, a measurement of the absolute value of the capacitance would also measure changes to the capacitances due to tilting or a change in spacing due to lack of rigidity of the arrangement.

In addition to the capacitive determination of the angle of rotation, optical methods are also possible. For this, discs with overlapping, partially transmissive structures, such as indented edges, are provided, and the overlapping or the offset is determined by the transmission of the two discs from the intensity of the light transmitted, with an offset of the discs resulting in a reduction in the free cross-section, which is optionally evaluated relative to a reference beam.

Evaluation electronics, which may be constructed in the manner of an RFID, can be attached to the two discs in each case on top and/or underneath. The data are read out in contact-free manner; the entire disc system turns jointly with the measuring shaft.

The motor used should offer the possibility of measurement with precisely defined rotational speed. This can be achieved with commercially obtainable stepper motors, or a commercial d.c. motors with built-in rotational speed regulator is used.

A particularly compact, robust and simple construction is illustrated in FIG. 6. Here the coupling coil 8, which interacts with the field coil 7 which is fixed on the motor or housing 16 or support 21 and inductively picks up the energy required for measuring, is integrated in one of the two measuring-sensor parts 17 or 18. The parallel measuring-sensor parts 17, 18 bear on the sides facing each other detector units, in particular the structures illustrated in FIG. 5 for capacitive measurement of the angle of rotation. The required bridge circuit and electronics 24 are realised on the measuring-sensor parts 17, 18. The measured values are read out after modulation of the coil signal via the field coil. The coils can of course be attached analogously to the lower measuring-sensor part 18, and the interaction then takes place with field coils 7 located underneath which are mounted in fixed manner on the housing 16. According to the invention, the mounting of the measuring shaft 25 takes place on the motor side at least above the torsion element 2.

The invention claimed is:

1. A rotational viscometer, comprising:
   a measuring shaft being rotated at a specified, rotational speed and having an upper shaft part and a lower shaft part;
   a motor for driving said measuring shaft;
   a measuring part carried by said measuring shaft and for being lowered into a sample;
   a detection unit for determining a torsion angle of said measuring part relative to a driven part of said measuring shaft;
   a twistable element incorporated into said measuring shaft between said upper shaft part and said lower shaft part, said twistable element carrying said lower shaft part of said measuring shaft, which carries said measuring part, said twistable element being rigid in an axial direction of said measuring shaft;
   an evaluation device; and
   said detection unit being movable jointly with said measuring shaft and determines a relative twisting or torsion angle between said upper shaft part disposed on a motor side with respect to said twistable element and said lower shaft part disposed on a measuring-part side, said detection unit supplying output signals to said evaluation device as a basis for determining a viscosity of the sample.

2. The rotational viscometer according to claim 1, wherein:
   said twistable element is selected from the group consisting of a flexural pivot and a torsion rod; and
   said detection unit is selected from the group consisting of an inductive measuring sensor, a capacitive measuring sensor and an optical measuring sensor.

3. The rotational viscometer according to claim 1, wherein said detection unit has two opposing measuring-sensor parts which cooperate with one another, a first of said measuring-sensor parts being connected to said upper shaft part of said measuring shaft which is on the motor side and a second of said measuring-sensor parts being connected to said lower shaft part of said measuring shaft which is on the measuring-part side.

4. The rotational viscometer according to claim 3, wherein said two measuring-sensor parts are fastened in each case to one of said upper and lower shaft parts in a vicinity of said twistable element.

5. The rotational viscometer according to claim 3, further comprising a flexural pivot having first and second sleeves for being twisted relative to one another, one of said two measuring-sensor parts is fastened to a free end of said first sleeve and another of said two measuring-sensor components is fastened to a free end of said second sleeve.

6. The rotational viscometer according to claim 1,
wherein said detector unit is a capacitive detector unit having disc-shaped, capacitor plates, opposing capacitor surfaces of said capacitor plates being coated with metal layers which form radially extending surface regions or crosspieces; and
further comprising a measuring unit for determining changes in a capacitance of a capacitor formed by said capacitor plates during a course of mutual rotation of said capacitor plates relative to each other.

7. The rotational viscometer according to claim 6, wherein in each case said capacitor surfaces are segmented or intermesh in a finger-shape on each of said capacitor plates.

8. The rotational viscometer according to claim 3, further comprising a transmit component selected from the group consisting of a transceiver component and a transmitter supported by one of said measuring-sensor parts for picking up energy necessary for measuring, which takes place via an air gap, and for emitting measuring signals to a transceiver on an equipment side, which takes place via an air gap.

9. The rotational viscometer according to claim 3, further comprising coupling coils for inductive coupling-in of energy or measurement data transmission and supported by at least one of an upper one of said measuring-sensor parts, said upper shaft part, or said lower shaft part, said coupling coils cooperating with coupling coils or field coils located on a stand, a housing or a support of the rotational viscometer.

10. The rotational viscometer according to claim 9, wherein at least one of said twistable element, said coupling coils or said measuring-sensor parts are disposed at least partially or in their entirety beneath a space provided for a mounting of said measuring shaft or said upper shaft part on the motor side.

11. The rotational viscometer according to claim 1, wherein said twistable element is formed to be rigid in the axial direction of said measuring shaft and is formed to be as rigid as possible against tilting in a radial direction.

12. The rotational viscometer according to claim 1, further comprising a transmitter, output signals of said detector unit are transmitted via said transmitter in a contact-free manner or via an air gap to said evaluation unit disposed on a housing side, or in that values determined by said detection unit are processed therein and resulting viscosity values or processed measured values for determining the viscosity values are transmitted via said transmitter in a contact-free manner or via an air gap to said evaluation unit.

13. The rotational viscometer according to claim 6, wherein said measuring unit for determining changes in capacitance is supported by one of said two measuring-sensor parts and supplies measured values to a coupling coil for transmission to a field coil.

14. The rotational viscometer according to claim 1, wherein said twistable element is incorporated into said measuring shaft in a section adjacent to said motor.

15. The rotational viscometer according to claim 3, wherein:
said two opposing measuring-sensor parts are selected from the group consisting of two capacitor plates, two coils, and two screens having light holes formed therein;
said first measuring-sensor part is connected directly to said upper shaft part; and
said second measuring-sensor part is connected directly to said lower shaft part.

16. The rotational viscometer according to claim 4, wherein said first measuring-sensor part is fastened immediately above said twistable element and said second measuring-sensor part is fastened immediately below said twistable element.

17. The rotational viscometer according to claim 8, wherein said transmit component is supported by an upper one of said measuring-sensor parts disposed on the motor side.

18. The rotational viscometer according to claim 8, wherein said transmit component is supported by said upper shaft part.

19. The rotational viscometer according to claim 6, further comprising at least one metal layer forming said capacitor surfaces and is applied to each of said capacitor plates.

20. The rotational viscometer according to claim 6, wherein said capacitor surfaces which are formed on said capacitor plates are connected into a bridge circuit.

* * * * *